United States Patent [19]

Love

[11] Patent Number: 5,716,399
[45] Date of Patent: Feb. 10, 1998

[54] METHODS OF HEART VALVE REPAIR

[75] Inventor: Jack W. Love, Santa Barbara, Calif.

[73] Assignee: Cardiomend LLC, Santa Barbara, Calif.

[21] Appl. No.: 539,971

[22] Filed: Oct. 6, 1995

[51] Int. Cl.$^6$ .................................................. A61F 2/24
[52] U.S. Cl. ............................................................. 623/2
[58] Field of Search ................................. 623/2, 900, 901

[56] References Cited

U.S. PATENT DOCUMENTS

| | | |
|---|---|---|
| 3,320,972 | 5/1967 | High et al. . |
| 3,655,306 | 4/1972 | Ross et al. . |
| 4,470,157 | 9/1984 | Love . |
| 4,561,129 | 12/1985 | Arpesella ........................... 623/2 |
| 4,731,075 | 3/1988 | Gallo Mezo et al. . |
| 4,960,424 | 10/1990 | Grooters . |
| 5,147,391 | 9/1992 | Lane . |
| 5,156,621 | 10/1992 | Navia et al. . |
| 5,163,955 | 11/1992 | Love et al. . |
| 5,197,979 | 3/1993 | Quintero et al. . |
| 5,258,021 | 11/1993 | Duran . |
| 5,326,370 | 7/1994 | Love et al. . |
| 5,326,371 | 7/1994 | Love et al. . |
| 5,336,258 | 8/1994 | Quintero et al. . |
| 5,352,240 | 10/1994 | Ross . |
| 5,358,518 | 10/1994 | Camilli ............................... 623/2 |
| 5,370,685 | 12/1994 | Stevens . |
| 5,376,112 | 12/1994 | Duran . |
| 5,376,113 | 12/1994 | Jansen ............................... 623/2 |
| 5,411,552 | 5/1995 | Andersen et al. . |
| 5,425,741 | 6/1995 | Lemp et al. . |
| 5,449,384 | 9/1995 | Johnson . |
| 5,480,424 | 1/1996 | Cox . |
| 5,503,638 | 4/1996 | Cooper et al. . |
| 5,509,930 | 4/1996 | Love ................................. 623/2 |

FOREIGN PATENT DOCUMENTS

| | | |
|---|---|---|
| B-85074/91 | 7/1994 | Australia . |
| 0 581 233 A1 | 2/1994 | European Pat. Off. . |
| 2399832 | 9/1979 | France . |
| WO 92/03990 | 3/1992 | WIPO . |
| 9212690 | 8/1992 | WIPO . |
| WO 92/13502 | 8/1992 | WIPO . |
| WO 93/18721 | 9/1993 | WIPO . |
| WO 95/16411 | 6/1995 | WIPO . |

OTHER PUBLICATIONS

Senning Å: Fascia lata replacement of aortic valves. J. Thorac Cardiovasc Surg 1967; 54–465–470.

Chauvaud S, Jebara V, Chachques J–C, Asmar BE, Mihaileanu S, Perier P, Dreyfus G, Relland J, Couetil J–P, Carpentier A: Valve extension with glutaraldehyde–preserved antologuous pericardium. J Thorac Cardiovasc Surg 1991; 102:171–178.

(List continued on next page.)

Primary Examiner—Michael J. Milano
Attorney, Agent, or Firm—Lyon & Lyon LLP

[57] ABSTRACT

A method for repairing a heart valve comprising steps of sizing an annulus of a heart; harvesting tissue; cutting a trefoil pattern matched to the size of the annulus from the harvested tissue; forming a valve having at least one leaflet from said trefoil pattern, where the valve has a base with an edge portion of tissue extending around an outer periphery thereof; and suturing the edge portion to the exposed annulus; also disclosed is a method of repairing a heart valve comprising steps of: sizing an annulus of a heart at a repair site; harvesting tissue; cutting a trefoil pattern from the harvested tissue specific to the size of the annulus; providing first and second formers which are specific to the size of the annulus of the valve, forming a tri-leaflet valve from said trefoil pattern by engaging blades of said first former to corresponding blades of said second former with said trefoil pattern sandwiched therebetween; exposing an edge portion of tissue extending around an outer periphery of a base of the valve; moving the formers with the trefoil pattern sandwiched therebetween to a position which is proximate to the repair site; suturing the exposed edge portion to the annulus; and withdrawing the formers from the repair site.

27 Claims, 13 Drawing Sheets

OTHER PUBLICATIONS

Duran C, Kumar, Gometza B, Al Halees Z: Indications and limitations of aortic valve reconstruction. Ann Thorac Surg 1991; 52:447–454.

Love CS: An alternate method for applying a Dacron cover to a Delrin bioprosthetic heart valve stent. Proceedings of the Third Southern Biomedical Engineering Conference Pergamom Press 1984; 30–37.

Love JW, Calvin JH, Phelan RF, and Love CS: Rapid intraoperative fabrication of an autogenous tissue heart valve: a new technique. Proceedings of the Third International Symposium on Cardiac Bioprostheses. New York: York Medical Books; 1986; 691–698.

Love JW, Love CS, Calvin JH, and Phelan RF: Degenerative calcification in tissue valves—a metabolic/hemodynamic or immunological problem? Abstract published for the first scientific meeting of the International Association for Cardiac Biological Implants, Chicago, Illinois, Apr. 5, 1987.

Love JW, Calvin JH, Phelan RF, and Love CS: The autogenous tissue heart valve. Experience with pericardium. Proceedings of the International Symposium of the Austrian Society for Thoracic and Cardiovascular Surgery as a Heart Valve Substitute. Is it Living up to its Promise? Symbion, Inc., Salt Lake City, Utah, 1989; 31–40.

Love CS and Love JW: The autogenous tissue heart valve: current status. J Cardiac Surg 1991; 6: 499–507.

Love JW, Disc of Chauvaud S., Jebara V, Chachques J–C, et al: Valve extension with glutaraldehyde-preserved autologous pericardium. Results in mitral valve repair. J Thorac Cardiovasc Surg 1991; 102:171–178.

Love JW, Disc of Gott JP, Pan–Chih, Dorsey LMA, et al: Calcification of porcine valves: a successful new method of antimineralization. Ann Thorac Surg 1992; 53:207–216.

Love CS, Calvin JH and Love JW: Improved bioprosthetic heart valve durability. ASAIO 1992 Abstracts, p.32.

Love CS, Love JW, and Breznock EM: Autogenous tissue valve replacement in the canine. ASAIO 1992 Abstracts, p.32.

Love JW, Schoen FJ, Breznock EG, Shermer SP, Love CS: Experimental evaluation of an autologous tissue heart valve. J Heart Valve Dis 1992; 1:232–242.

Love JW: Autologous Tissue Heart Valves, Austin, Texas: Landes Publishing Company; 1993.

Love JW, Willems PW, and Love CS: An autologous tissue bioprosthetic heart valve. In Gabbay G, Fratgr RWM, eds. New Horizons and the Future of Heart Valve Bioprostheses. Austin, TX: Silent Partner, Inc.: 1944: 135–141.

METHODS OF HEART VALVE REPAIR

BACKGROUND OF THE INVENTION

This invention relates generally to methods of heart valve repair. More specifically, this invention relates to methods of heart valve repair which are standardized and thus more easily replicated in the limited time available while the patient is on the operating table.

It has been possible to replace heart valves for thirty-five years, since the advent of the heart-lung machine and various mechanical and tissue heart replacement heart valves designed by surgeons and engineers.

The concept of repairing, rather than replacing, diseased heart valves began with the work of Professor Åke Senning of Zurich in 1960. (Senning Å:Fascia lata replacement of aortic valves. J Thorac Cardiovasc Surg 1967; 54:465–470). Senning used autologous fascia lata to fashion both aortic valve repairs and replacements with a freehand technique, but subsequently abandoned his method by 1970 because of valve failures from thickening and shrinkage of the fresh, untreated tissue.

The concept of valve repair with autologous tissue was resurrected by Professor Alain Carpentier of Paris. Beginning in 1980, he began work with the repair of mitral valve leaflets damaged by rheumatic heart disease, using gusset patches of autologous pericardium treated with a brief immersion in glutaraldehyde. In 1991, Carpentier reported a series of 64 patients who had mitral leaflet augmentation by this technique from 1980 to 1989, with excellent results. (Chauvaud S., Jebara V., Chachques J.-C., Asmar B. E., Mihaileanu S., Perier P., Dreyfus G., Relland J., Couetil J.-P., Carpentier A:Valve extension with glutaraldehyde-preserved antologuous pericardium. J Thorac Cardiovasc Surg 1991; 102:171–178). Importantly, he was able to report that the autologous tissue treated with glutaraldehyde did not thicken or shrink or calcify, up to ten years after implantation for repair. In addition to this method for leaflet augmentation, Carpentier employs a combination of annuloplasty, leaflet resection, and chordal shortening and re-implantation techniques to repair mitral valves.

Duran has used autologous pericardium treated with a brief immersion in glutaraldehyde for repair of diseased aortic valves, with good results, including lack of calcification. (Duran C., Kumar N., Gometza B., Al Halees Z:Indications and limitations of aortic valve reconstruction. Ann Thorac Surg 1991; 52:447–454).

A problem with all these approaches, however, is that they were not standardized and thus could not easily be replicated in the limited time available while the patient was on the operating table. Although, as described in U.S. Pat. Nos. 5,326,371; 5,163,955; 5,326,370; and 4,470,157, all of which are incorporated by reference herein as though set forth in full, standardized approaches to valve replacement (in contrast to valve repair) have recently become available, such approaches involve the use of a stent.

The problem with a stent-mounted prosthesis is that the stent occupies space and thereby reduces the effective orifice area of the valve. Another disadvantage is that a stent is foreign material, and the prosthesis must be replaced, in most cases, if it becomes infected. Prosthetic valve infection is not common, but when it occurs, it is a catastrophic complication.

Accordingly, it is an object of the invention to provide a method of and apparatus for valve repair which overcomes the disadvantages of the prior art.

PRIOR PUBLICATIONS

The following publications all relate to or describe prior work performed by Dr. Jack Love, the inventor herein, in the area of autogenous tissue cardiac valves:

(1) Love CS: An alternate method for applying a Dacron cover to a Delrin bioprosthetic heart valve stent. Proceedings of the Third Southern Biomedical Engineering Conference. Pergamom Press 1984; 30–37.

(2) Love J. W., Calvin J. H., Phelan R. F., and Love C. S.: Rapid intraoperative fabrication of an autogenous tissue heart valve: a new technique. Proceedings of the Third International Symposium on Cardiac Bioprostheses. New York: York Medical Books; 1986; 691–698.

(3) Love J. W., Love C. S., Calvin J. H., and Phelan R. F.: Degenerative calcification in tissue valves—a metabolic/hemodynamic or immunological problem? Abstract published for the first scientific meeting of the International Association for Cardiac Biological Implants, Chicago, Ill., Apr. 5, 1987.

(4) Love J. W., Calvin J. H., Phelan R. F., and Love C. S.: Experimental evaluation of an autogenous tissue heart valve. Poster presentation at the Fourth International Symposium on Cardiac Bioprostheses, San Diego, Calif., Apr. 15, 1988.

(5) Love J. W., Calvin J. H., Phelan R. F., and Love C. S.: The autogenous tissue heart valve. Experience with pericardium. Proceedings of the International Symposium of the Austrian Society for Thoracic and Cardiovascular Surgery as a Heart Valve Substitute. Is it Living up to its Promise? Symbion, Inc., Salt Lake City, Utah, 1989; 31–40.

(6) Love CS and Love J. W.: The autogenous tissue heart valve: current status. J Cardiac Surg 1991; 6:499–507.

(7) Love J. W., Disc of Chauvaud S., Jebara V., Chachques J. C., et al: Valve extension with glutaraldehyde-preserved autologous pericardium. Results in mitral valve repair. J Thorac Cardiovasc Surg 1991; 102:171–178.

(8) Love J. W., Disc of Gott J. P., Pan-Chih, Dorsey LMA, et al: Calcification of porcine valves: a successful new method of antimineralization. Ann Thorac Surg 1992; 53:207–216.

(9) Love C. S., Calvin J. H. and Love J. W.: Improved bioprosthetic heart valve durability. ASAIO 1992 Abstracts, p.32.

(10) Love C. S., Love J. W., and Breznock E. M.: Autogenous tissue valve replacement in the canine. ASAIO 1992 Abstracts, p.32.

(11) Love J. W., Schoen F. J., Breznock E. G., Shermer S. P., Love CS: Experimental evaluation of an autologous tissue heart valve. J Heart Valve Dis 1992; 1:232–242.

(12) Love J. W.: Autologous Tissue Heart Valves, Austin, Tex.: Landes Publishing Company; 1993.

(13) Love J. W., Willems P. W., and Love CS: An autologous tissue bioprosthetic heart valve. Paper presented at International Society of Cardiac Vascular Surgery by J. W. Love, Lisbon, Portugal, Sep. 15, 1993.

(14) Love J. W., Willems P. W., and Love CS: An autologous tissue bioprosthetic heart valve. In Gabbay G., Fratgr R. W. M., eds. New Horizons and the Future of Heart Valve Bioprostheses. Austin, Tex.: Silent Partner, Inc.: 1994: 135–141.

All of these publications and/or presentations are hereby incorporated by reference herein as though fully set forth in full.

BRIEF DESCRIPTION OF THE DRAWINGS

In all the aforementioned figures, like elements are referenced with like identifying numerals.

SUMMARY OF THE INVENTION

To achieve the foregoing objects, and in accordance with the purpose of the invention as broadly described herein, there is provided a method of heart valve repair comprising the following steps:

(a) sizing an annulus of a heart;

(b) harvesting tissue;

(c) cutting a trefoil pattern out of the harvested tissue which is specific to the size of the annulus;

(d) forming a tri-leaflet valve from the trefoil pattern, the valve having a base with an edge portion extending around an outer periphery thereof; and (e) suturing the edge portion of the valve to the annulus.

The trefoil pattern is a one-piece geometric shape having three-way radial symmetry, i.e., wherein each 120° sector of the pattern is substantially identical in shape.

In one embodiment of the subject invention, the trefoil pattern is molded into the tri-leaflet valve manually by the surgeon. In a second embodiment, the valve is formed using a pair of formers which are capable of being configured in an engaging relationship with the trefoil pattern sandwiched there between.

In a variant of the subject invention, the trefoil pattern is cut from the harvested tissue using a tissue cutting die. Another variant involves containing the pair of formers and/or tissue cutting die in a size specific prefabricated kit. A third variant involves using autologous tissue taken from the patient. A fourth variant involves using a pledger formed from a bio-compatible material to reinforce the edge portion at the base of the valve.

DESCRIPTION OF THE PREFERRED EMBODIMENTS

The subject invention is particularly suited for aortic and pulmonic valve repair.

Figure 1:
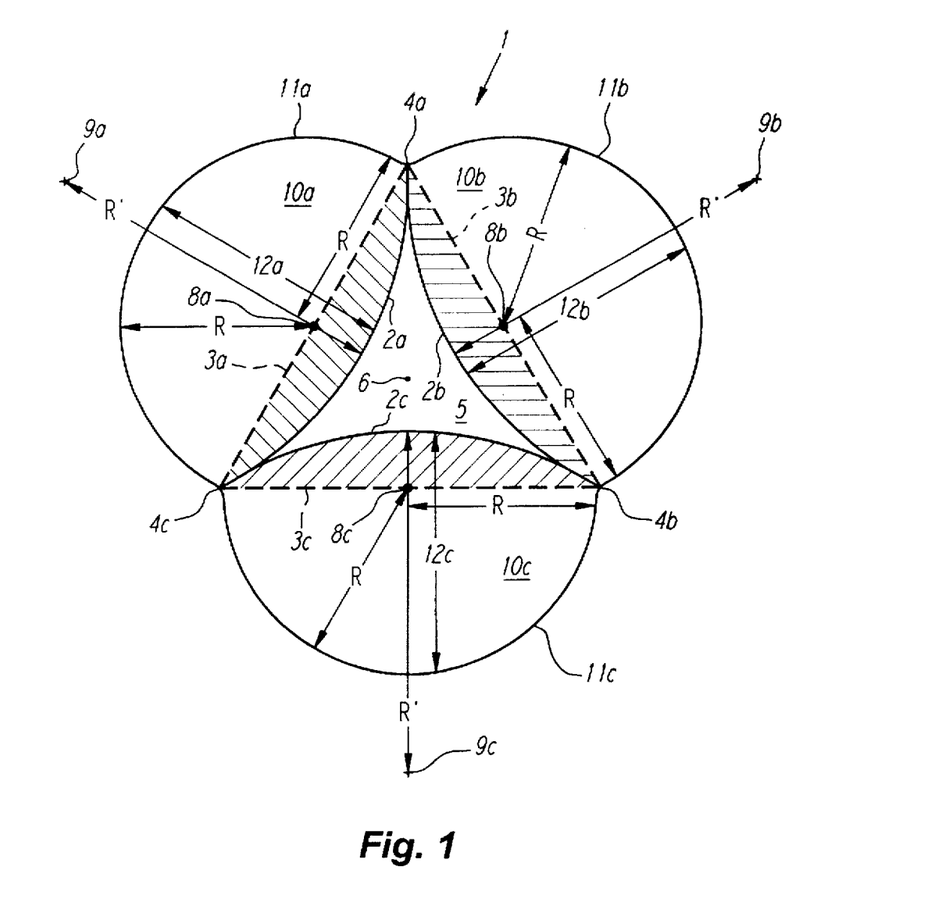
FIG. 1 illustrates the preferred trefoil tissue pattern for use with the subject invention.

The preferred tissue trefoil pattern of the subject invention is identified with numeral 1 in FIG. 1. As shown, the pattern has three-way radial symmetry about central point 6. Shown in phantom around central point 6 is an equilateral triangle having edges 3, which define the lines of coaption of the closed valve. The length of these edges defines the diameter of the final valve repair. For example, a valve annulus having a radius R requires that the length of these edges be 2R.

As shown, the pattern consists of three lobes, identified with numerals 10a, 10b and 10c. The outer peripheries of the three lobes is defined respectively by arcs 11a, 11b and 11c. The inner peripheries of the respective lobes are defined by arcs 2a, 2b and 2c. As shown, arcs 11a, 11b and 11c have a radius R defined in relation to the mid-points 8a, 8b and 8c of edges 3a, 3b and 3c of the equilateral triangle. Moreover, arcs 2a, 2b and 2c have a radius R' defined in relation to points 9a, 9b and 9c. The value of R' is preferably greater than R to avoid overlapping between adjacent arcs. However, as will be discussed, the value of R' has no maximal value.

As discussed, edges 3a, 3b and 3c form the lines of coaption of the closed valve. The cross-hatched areas shown in FIG. 1 define extra coaptive surfaces, the area of which is defined by R'. The greater the value of R', the smaller these areas of extra-coaption. Conversely, the smaller the value of R', the greater these areas of extra-coaption.

The trefoil pattern is used to form the tri-leaflet valve structure. Specifically, each lobe of the pattern will form one leaflet of the valve structure. In the final structure, the three leaflets of the valve meet at a central coaption point. The extra-coaptive surfaces shown in cross-hatch in FIG. 1 replicate nature in that they allow for the central coaption point of the tri-leaflet valve formed thereof to lie above the plane defined by the commissural points 4a, 4b and 4c.

The valve profile is a characteristic defined by the lobe length. The lobe length, as the name suggests, is the length of an individual leaflet in the tri-leaflet structure. In relation to FIG. 1, it is defined as the distance between the apexes of the arcs 2a, 2b and 2c, and the corresponding apexes of arcs 11a, 11b, and 11c. In FIG. 1, these lobe lengths are identified with numerals 12a, 12b and 12c. It will be appreciated that the longer the lobe length, the higher the profile of the tri-leaflet structure, while the shorter the lobe length, the smaller the profile of the tri-leaflet structure. Because the central coaption point in the final valve will be the point at which points 8a, 8b and 8c within segments 3a, 3b and 3c intersect, a minimum value for the lobe length is R, the radius of the valve annulus. It should be appreciated that the lobe length can be varied depending on R'.

It should be appreciated that the definition of trefoil pattern described herein encompass minor variations in the size and shape of the lobes thereof which do not affect valve function, and which arise from several factors, including minor variations in the thickness of the tissue and the fact that the valve annulus is not a perfect circle.

The preferred method of repairing a heart valve using this trefoil pattern comprises the following steps:

(a) sizing an annulus of the heart;

(b) harvesting tissue;

(c) cutting the trefoil pattern from the harvested tissue;

(d) forming a tri-leaflet valve from the trefoil pattern, the valve having a base with an edge portion extending around an outer periphery thereof; and (e) suturing the edge portion of the valve to the exposed annulus.

Additional preparatory steps may include opening the chest cavity to expose the heart, establishing the patient on cardiopulmonary bypass, and exposing the valve annulus by excising diseased valve leaflets.

Once this preparatory work has been accomplished, the next step is to size the annulus. This step is advantageously accomplished by inserting plugs of increasing size into the annulus until the plug having the size of the annulus is determined.

The next step involves harvesting tissue. It should be appreciated that a variety of tissues are possible, including autologous tissue, bovine tissue, or porcine tissue. Moreover, many types of autologous tissue can be used, including pericardial, fascia lata, and rectus sheath (the fibrous tissue enveloping the abdominal muscles). If autologous tissue is used, pericardium is preferred, because of its proximity to the heart and the site of valve repair, and also because of its structural similarity to natural heart valve tissue. Another advantage is that pericardium has an identifiable range of thicknesses, strengths, elastin and collagen content.

The next step, in the case in which autologous tissue is used, is to treat the tissue with glutaraldehyde in order to strengthen it and prevent it from thickening or shrinking after it has been implanted. For example, it has been found that immersion for about 10 minutes in a dilute glutaraldehyde solution, such as a 0.625% glutaraldehyde solution buffered to a Ph of 7.4 units with phosphate, produces acceptable results.

The next step involves cutting the tissue into the trefoil pattern. Advantageously, a tissue cutting die, matched to the size of the specific annulus involved, can be used for this purpose. Such a die can be formed from a razor sharpened blade which is precisely configured to form the outline of the trefoil pattern of FIG. 1 and which can be embedded in a frame of bio-compatible material, such as thermoplastic, teflon, polycarbonate, or polysulfone. Alternatively, a cutting instrument such as a diamond bladed knife or laser may be used.

Additional details describing the steps of exposing the valve annulus, harvesting autologous tissue from the patient, annulus sizing, glutaraldehyde treatment, and the use of tissue cutting dies are available in the aforementioned publications.

The next step involves forming a tri-leaflet valve structure from the trefoil pattern.

In a first embodiment, a pair of size specific formers is used, which are configured to engage one another, with the trefoil pattern sandwiched therebetween, in order to form the tri-leaflet valve structure.

Figure 2A:
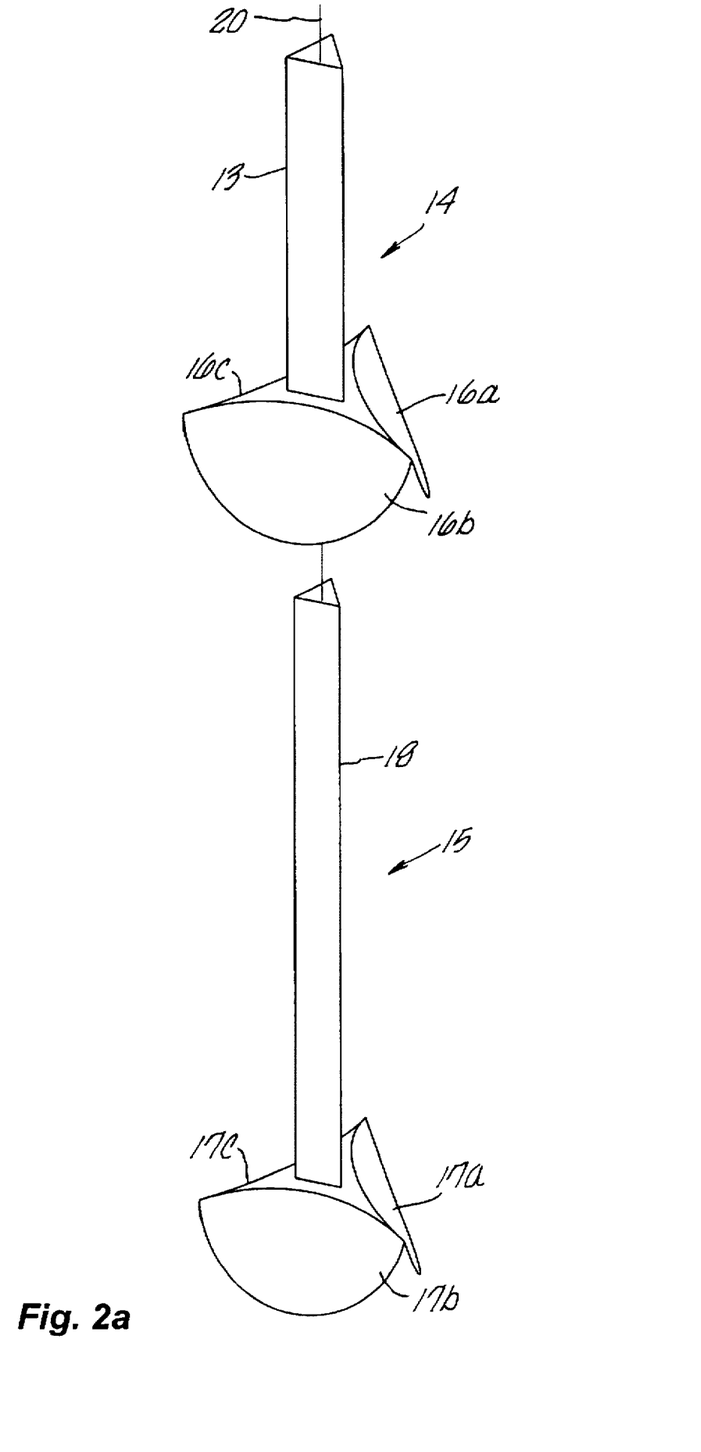
FIGS. 2a–2b illustrate side views of a first embodiment of upper and lower formers adapted for use in the subject invention.
Figure 2B:
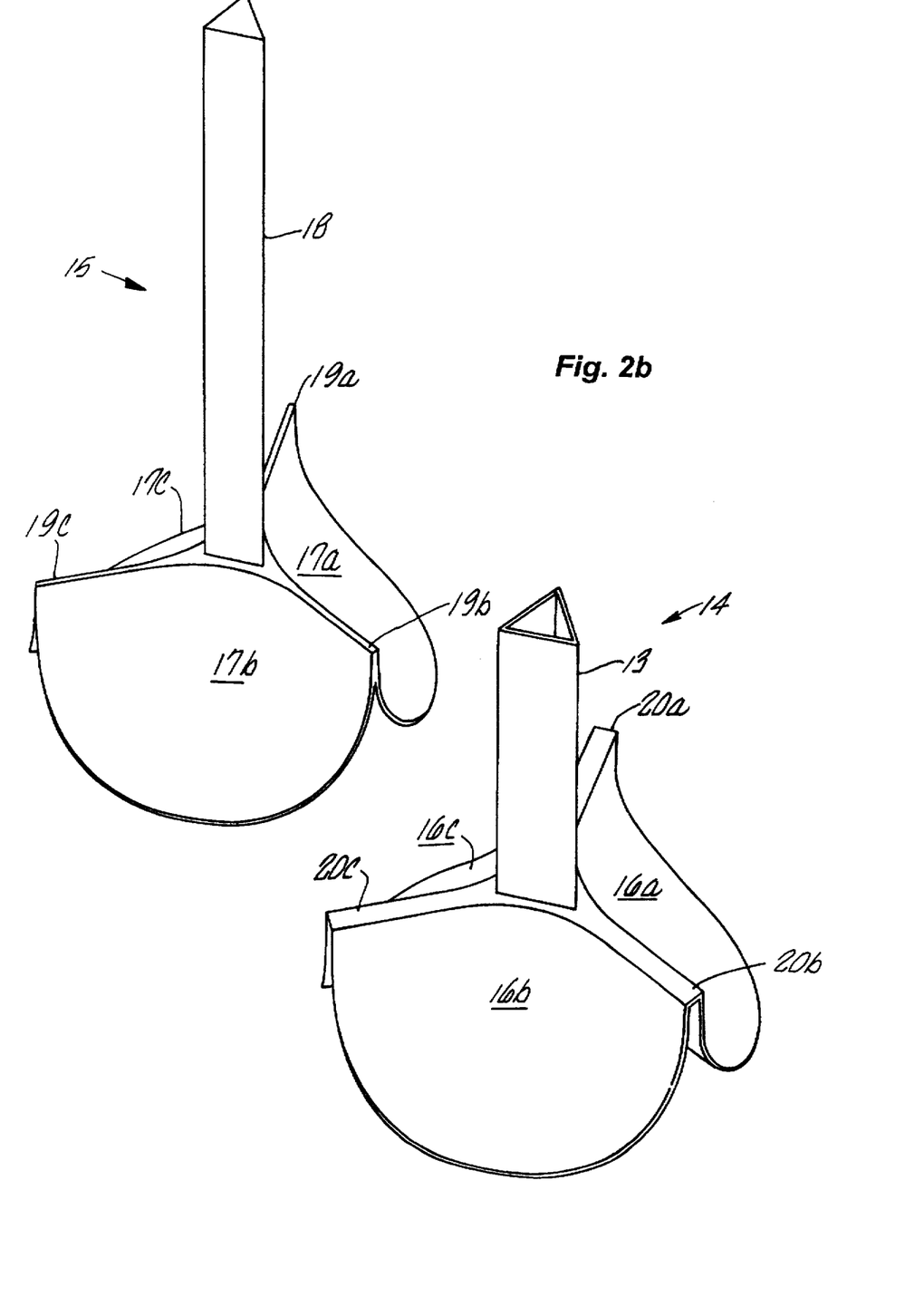

FIGS. 2a–2b illustrate advantageous embodiments of the upper former 14 and lower former 15. As shown, the upper former has a handle 13 which extends along axis 20, and which in cross-section, forms a hollow polygon. Attached to one end of handle 13 are three blades, identified with numerals 16a, 16b, and 16c, which extend away from the handle in directions which are at least partially orthogonal to the axis 20 of the handle, and which are spaced about 120° from one another.

Similarly, the lower former 15 has a handle 18 which also extends along axis 20, and which, in cross-section, forms a solid or hollow polygon (FIG. 2a illustrates an embodiment in which the cross-section of the handle 18 is hollow, while FIG. 2b illustrates an embodiment in which the cross-section is solid). Attached to one end of handle 18 are three blades, with numerals 17a, 17b, and 17c, which extend from the handle in directions which are at least partially orthogonal to the axis 20 of the handle, and which are spaced about 120° from one another.

Preferably, the blades of the upper former, 16a, 16b, and 16c, and the blades of the lower former, 17a, 17b, and 17c, are molded in three dimensions to the conformation of a partially closed tri-leaflet valve as shown in FIG. 2a.

Figure 3A:
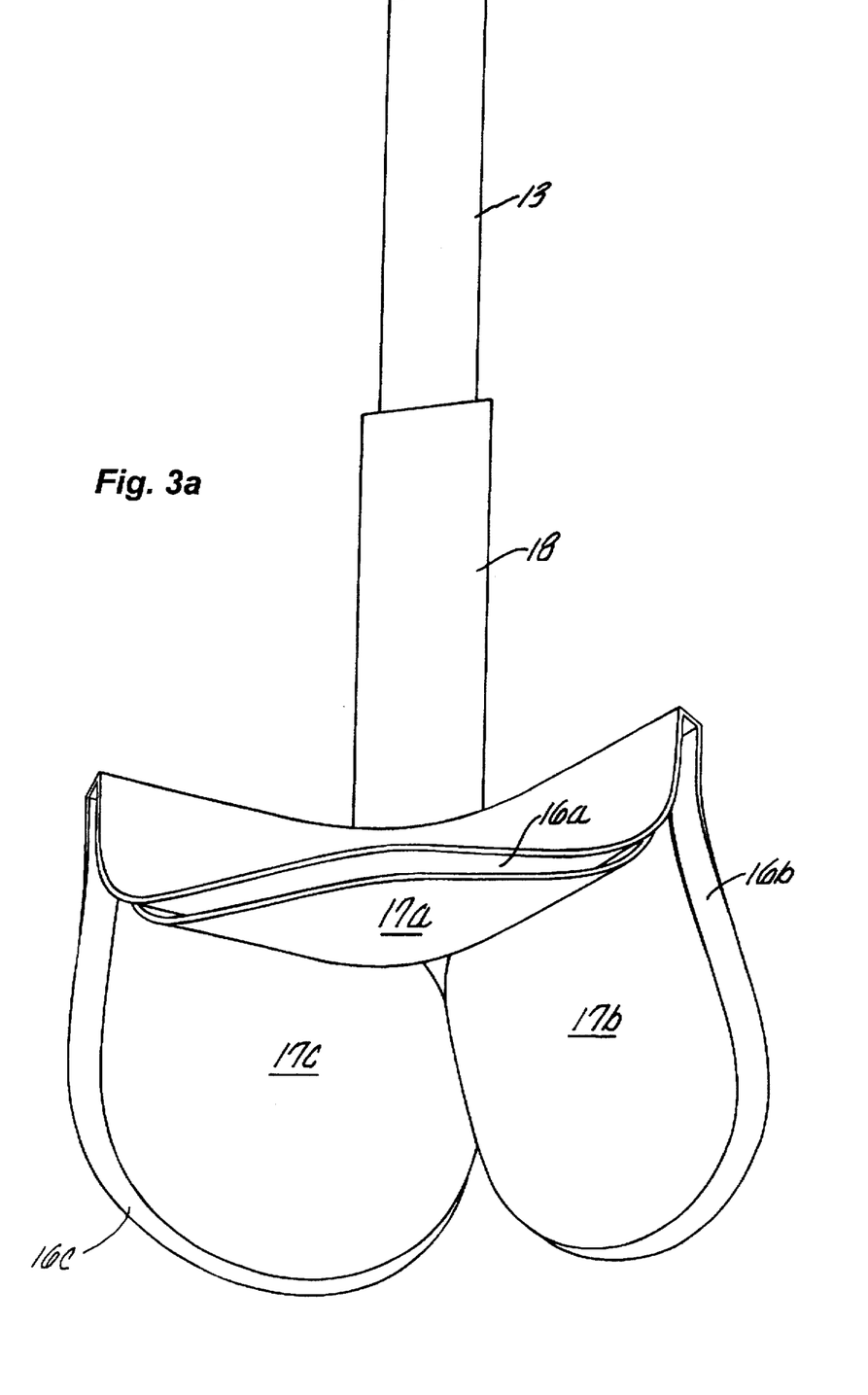
FIGS. 3a–3b illustrate views from below of the upper and lower formers of FIGS. 2a–2b.
Figure 3B:
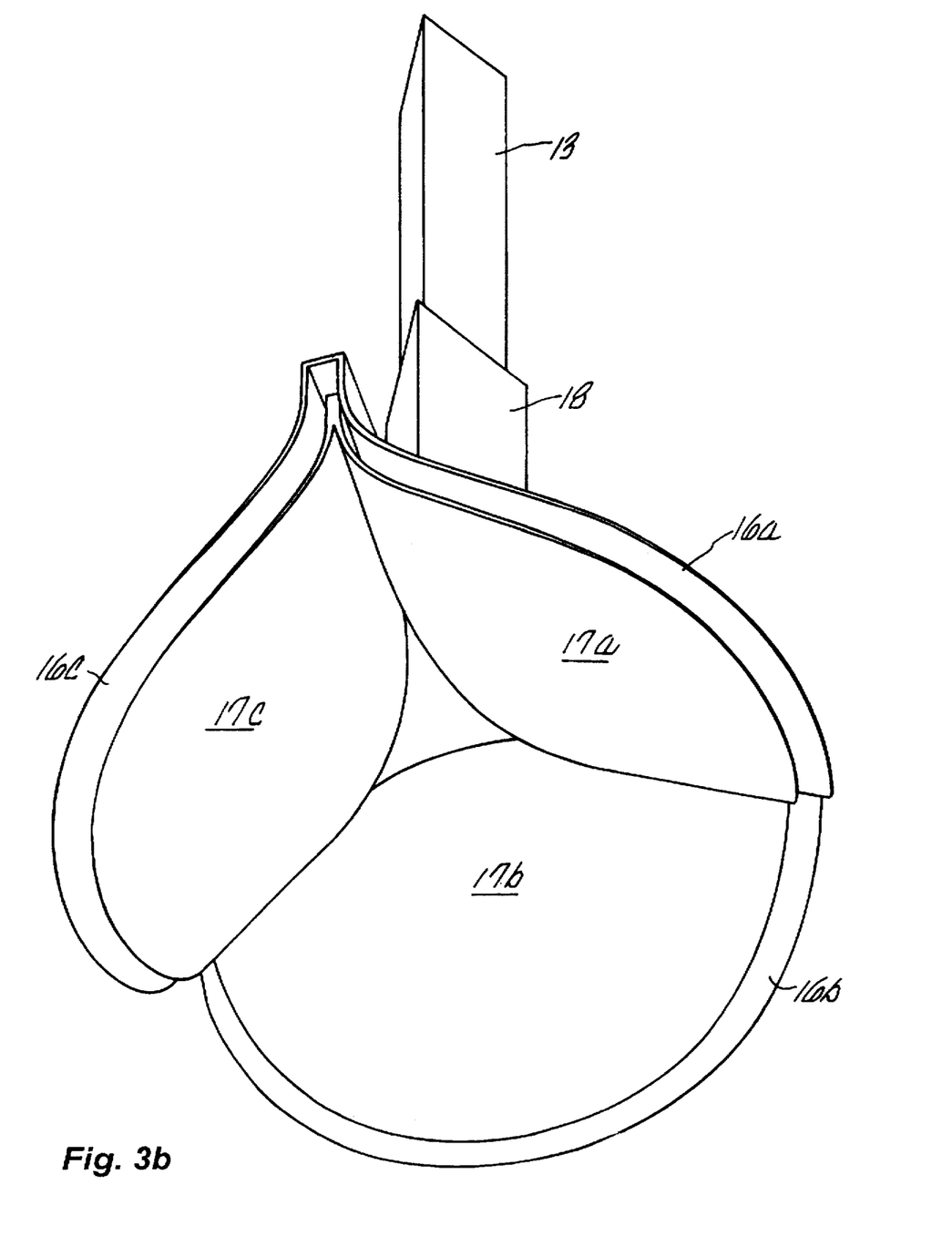

The size of the cross-section of handle 18 is preferably smaller than that of the handle 13 of the upper former, to allow the handle 18 to be inserted into the hollow portion of the handle 13 such that the blades thereof 17a, 17b and 17c can slidably engage corresponding ones of blades 16a, 16b, and 16c, as illustrated in FIGS. 3a–3b.

The cross-sectional shape of the handles should preferably be such as to allow for proper indexing of the formers in relation to one another. The triangular shape, such as that shown in the figures, facilitates this indexing because it prevents one handle from rotating relative to the other when the two are engaged. In general, any polygonal shape is appropriate as long as this indexing feature is provided.

Figure 4A:
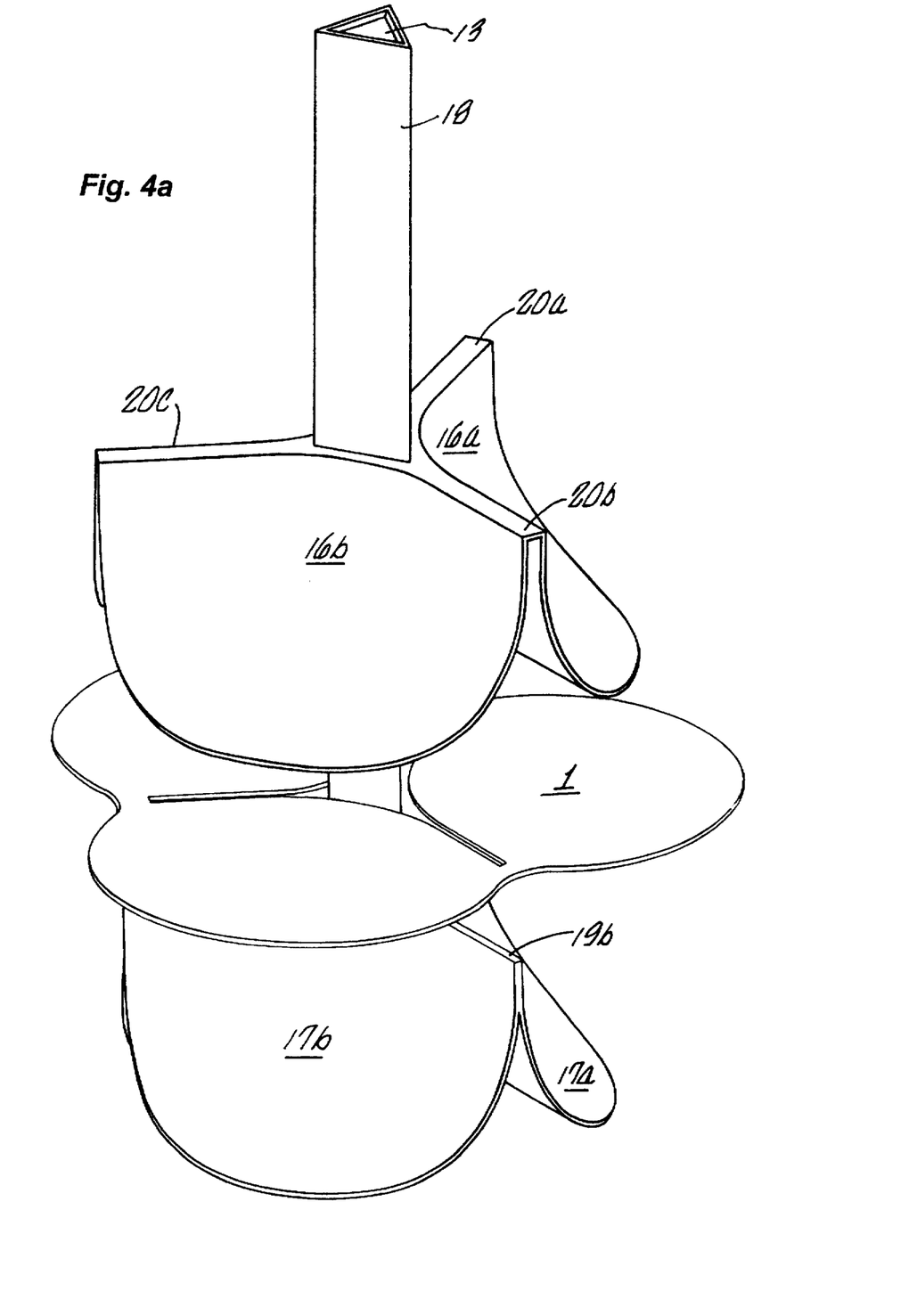
FIGS. 4a–4c illustrate partially exploded views of the upper and lower formers of FIGS. 2a–2b.

In operation, the handle 13 of the lower former is inserted through the aperture 5 of the trefoil pattern 1, and then into the hollow cross-section of the handle 18 of the upper former. The result is illustrated in FIG. 4a. The triangular shape of the handles causes the blades 17a, 17b, and 17c, to be automatically aligned with the corresponding blades 16a, 16b, and 16c of the upper former. It also causes the commissural areas 19a, 19b, and 19c of the lower former to be automatically aligned with the commissural areas 20a, 20b, and 20c, of the upper former.

Figure 4B:
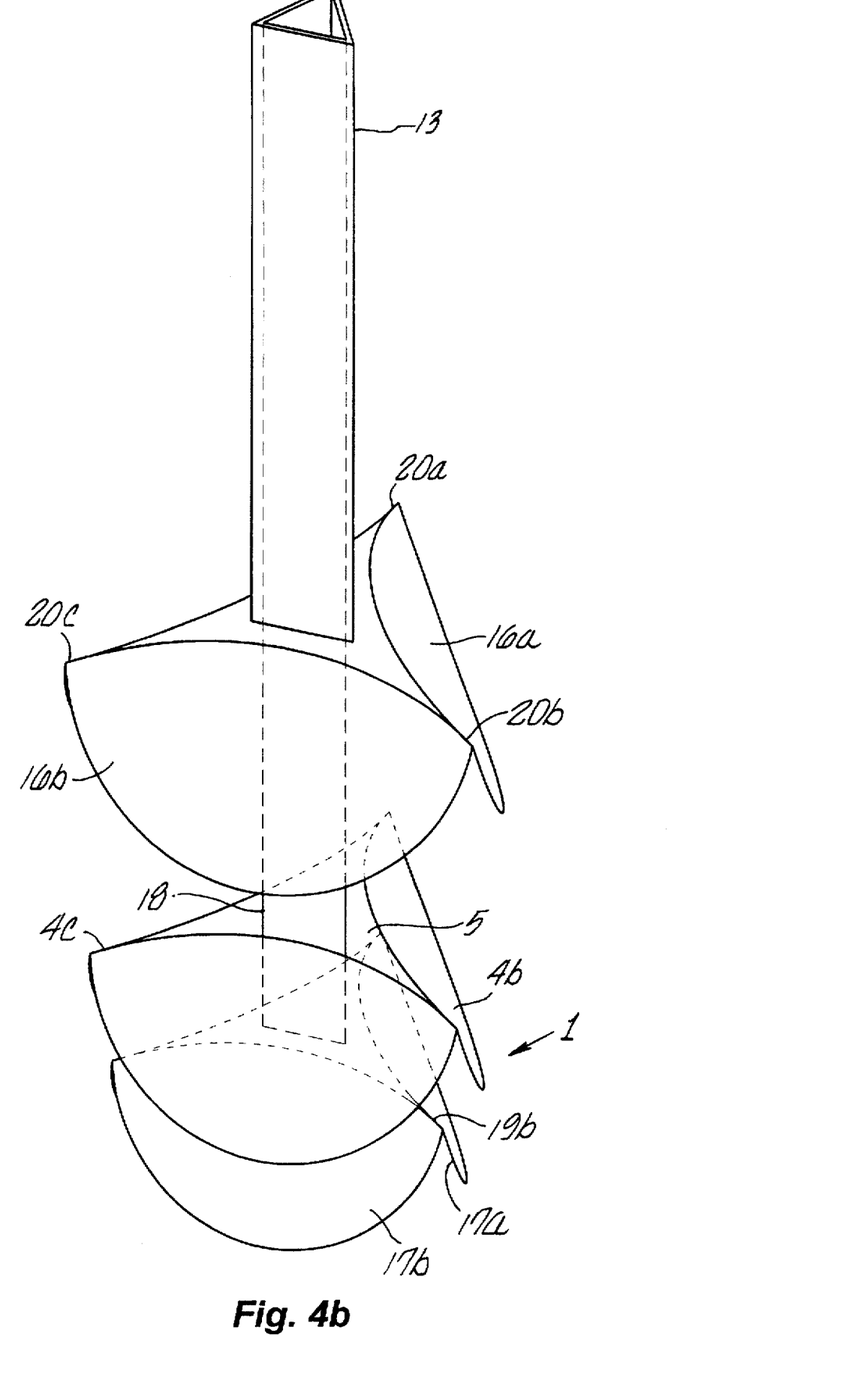

The lower former is then fully inserted into the upper former such that the trefoil pattern of tissue is sandwiched between the blades of the two formers. The blades of the two formers nest together, while the precut trefoil pattern of tissue is sandwiched between them. The result is that the trefoil pattern is molded into the tri-leaflet structure. This operation is illustrated in FIG. 4b.

Advantageously, the formers are constructed of a biocompatible material such as stainless steel, or plastic such as polycarbonate or acrylic. Moreover, each blade is advantageously configured to form a shape corresponding to one leaflet of the tri-leaflet valve. Accordingly, the blades are concave, and exhibit symmetry about a radial bisecting line extending from the handle through the middle of the blade.

Preferably, the blades 17a, 17b, and 17c of the lower former, and the blades 16a, 16b, 16c of the upper former, are configured to leave an exposed edge of tissue when the two formers have been placed in an engaging relationship with the tissue sandwiched therebetween. It has been found that an edge between 2–3 mm is appropriate. The step of suturing the tri-leaflet valve structure into the exposed annulus simply involves situating the two formers with the tissue sandwiched therebetween in proximity to the exposed annulus, and then suturing the exposed strip of tissue thereto, using either mattress sutures or continuous sutures.

For aortic or pulmonary valve repair, the line of sutures should follow a scalloped shape between commissures. The fringe of tissue is sutured to the remnant of the diseased valve that has been excised, and the geometry of the remnant, the annulus, establishes the geometry of the completed valve repair, obviating the need for a stent. Suturing is done by a continuous, distracted technique with monofilament suture that can be pulled tight after suturing, thus approximating the tissue trefoil to the valve annulus. Interrupted distracted sutures, either pledgeted or non-pledgeted, can be used in lieu of the continuous technique.

Once the suturing has been completed, the formers are withdrawn from the repair site. The upper former can be removed simply by withdrawing the same from the repair site while the lower former is kept in place.

Figure 4C:
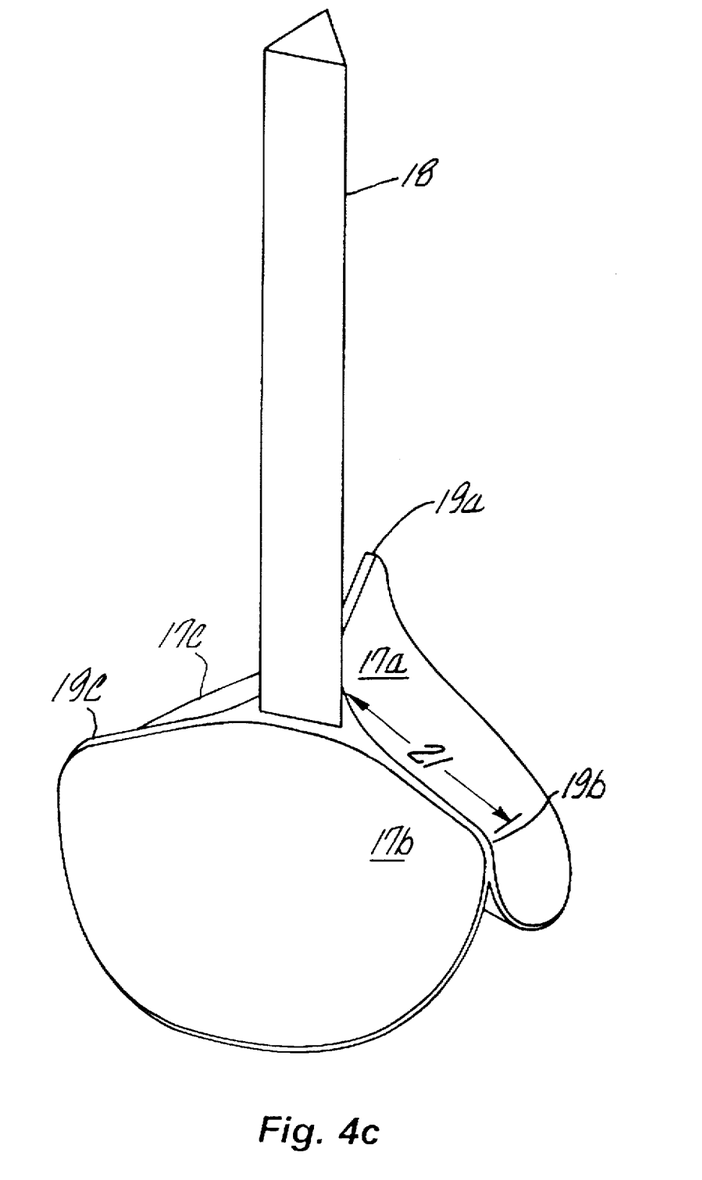

To facilitate easy removal of the lower former from the repair site, the features shown in FIG. 4c should be incorporated into the lower former. Specifically, the length of the commissural lines 19a, 19b, and 19c of the lower former, which length is identified in FIG. 4c with numeral 21, should be shorter than the corresponding length of the commissural lines of the central aperture of the trefoil pattern. That permits withdrawal of the lower former through the central orifice of the repaired valve.

Figure 4D:
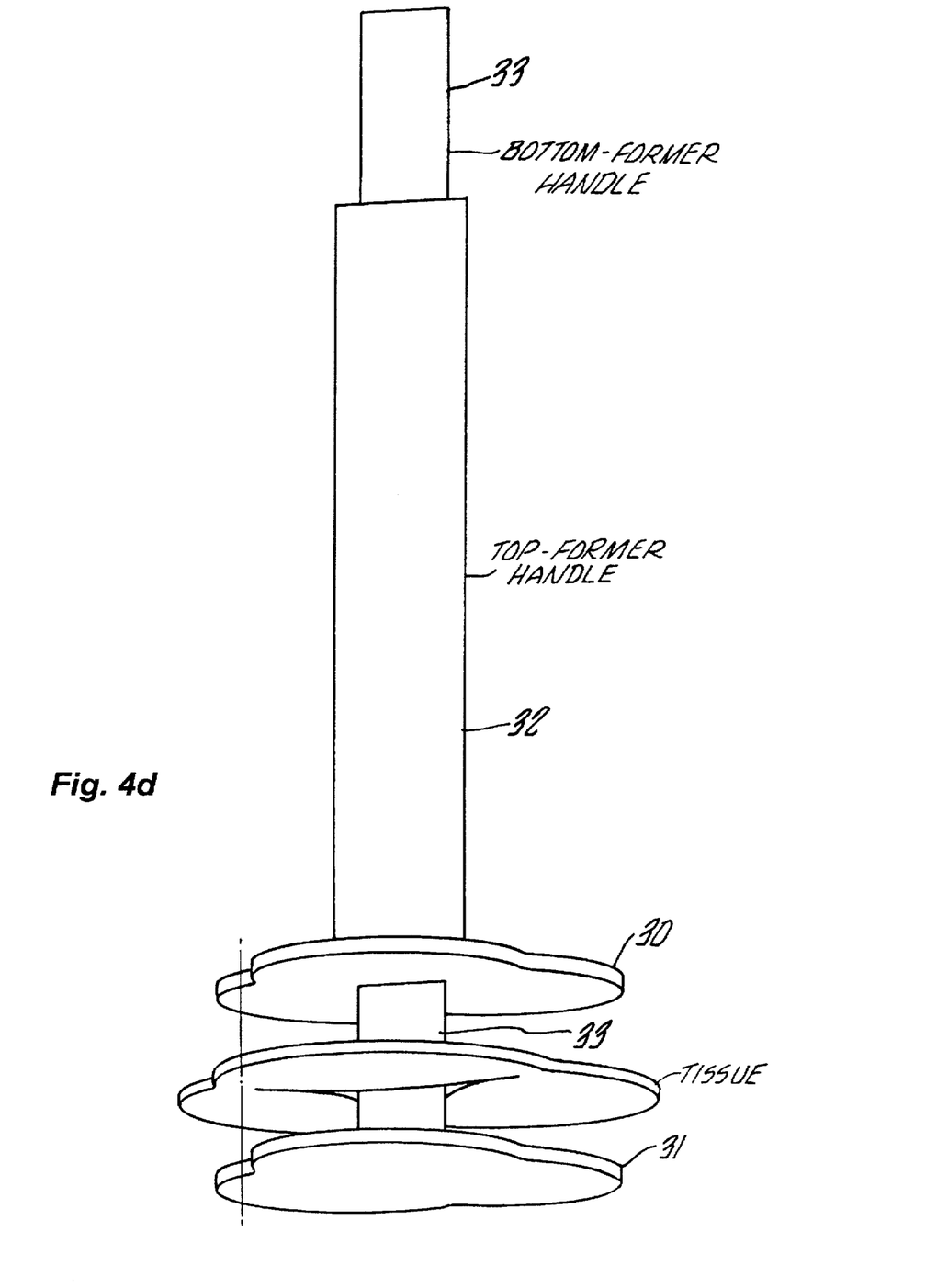
FIG. 4d illustrates a second embodiment of upper and lower formers adapted for use in the subject invention.

In a second embodiment, the forming step is performed manually by the surgeon using the apparatus illustrated in FIG. 4d. As shown, planar formers 30 and 31 are provided. Advantageously, these two formers are made of a transparent material, which is configured in a two-dimensional, planar shape. Also provided is handle 32 and pin 33. Advantageously, the formers are configured with holes, identified respectively with numerals 34 and 35, for passage therethrough of pin 33. Pin 33 has an end, identified with numeral 36, which advantageously engages, through a screw relationship or the like, end 37 of handle 32.

In this embodiment, the precut trefoil pattern 1 is sandwiched between the two planar formers 30 and 31. Pin 33 is then inserted through the hole 35 of former 31, the central aperture 5 of pattern 1, and the hole 34 of former 30 to engage the end 37 of handle 32. Preferably, the formers are configured to leave an exposed strip of about 2-3 mm of tissue, which is sutured to the annulus using a distracted technique, in which long loops of suture material are used to only loosely engage the strip to the annulus, and to allow the tissue to remain spaced from the annulus by about 6 inches.

When this has been accomplished, the handle 32 is disengaged from pin 33, and the handle 32, the lower former 31, and the pin 33 are removed from the repair site. Next, the upper former 30 is removed from the repair site. This sequence is employed to prevent the pin and lower former from falling into the heart, or left or right ventricles. The tissue trefoil prevents the upper former from falling into the heart. That is why the upper former is removed last.

This removal process is facilitated through use of the distracted technique of suturing described above, which enables the handle, formers, and pin to be removed from the repair site by withdrawing them through the network of distracted sutures.

The sutures are then closed, thus drawing the precut tissue to the annulus. The tissue is then molded into the shape of the tri-leaflet valve simply by pressing the tissue up against the annulus remnant. The shape of the remnant thus automatically molds the tissue into the desired shape. The geometry of this remnant is illustrated in FIG. 1 of Senning A:Fascia lata replacement of aortic valves. J Thorac Cardiovasc Surg 1967; 54:465–470, which is hereby fully incorporated by reference herein as though set forth in full.

A variant of the subject invention involves the use of a size specific pre-fabricated kit, in which is contained a size specific cutting die for use in forming the trefoil pattern for the prescribed valve size, and size specific upper and lower formers configured for the specific size of the valve involved. Another variant involves use of a second non-size specific kit, in which is contained tools for harvesting tissue from the patient, a basin for glutaraldehyde treatment thereof, and tools for sizing the annulus of the valve.

A third variant involves the use of a pledger for reinforcing the strip of tissue at the base of the tri-leaflet valve which is sutured into the exposed annulus.

Figure 5A:
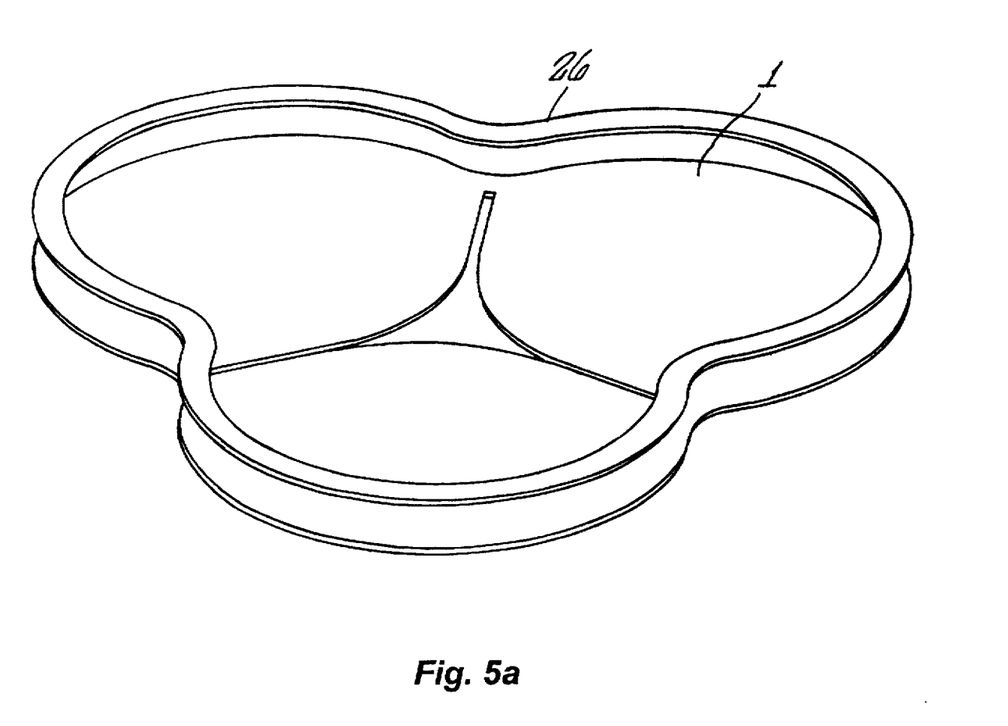
FIGS. 5a–5e illustrate the use of a continuous pledget reinforcing strip in the context of the subject invention.

FIG. 5a illustrates pledget 26 and trefoil pattern 1. As shown, the pledger follows the same general outline as the trefoil pattern, and thus is specific to the size of the valve annulus. Advantageously, the pledger is constructed of a flexible bio-compatible material such as thermoplastic or silicon, or a stiffened fabric such as TEFLON™ felt, DACRON™ felt, or DACRON™ velour.

Figure 5B:
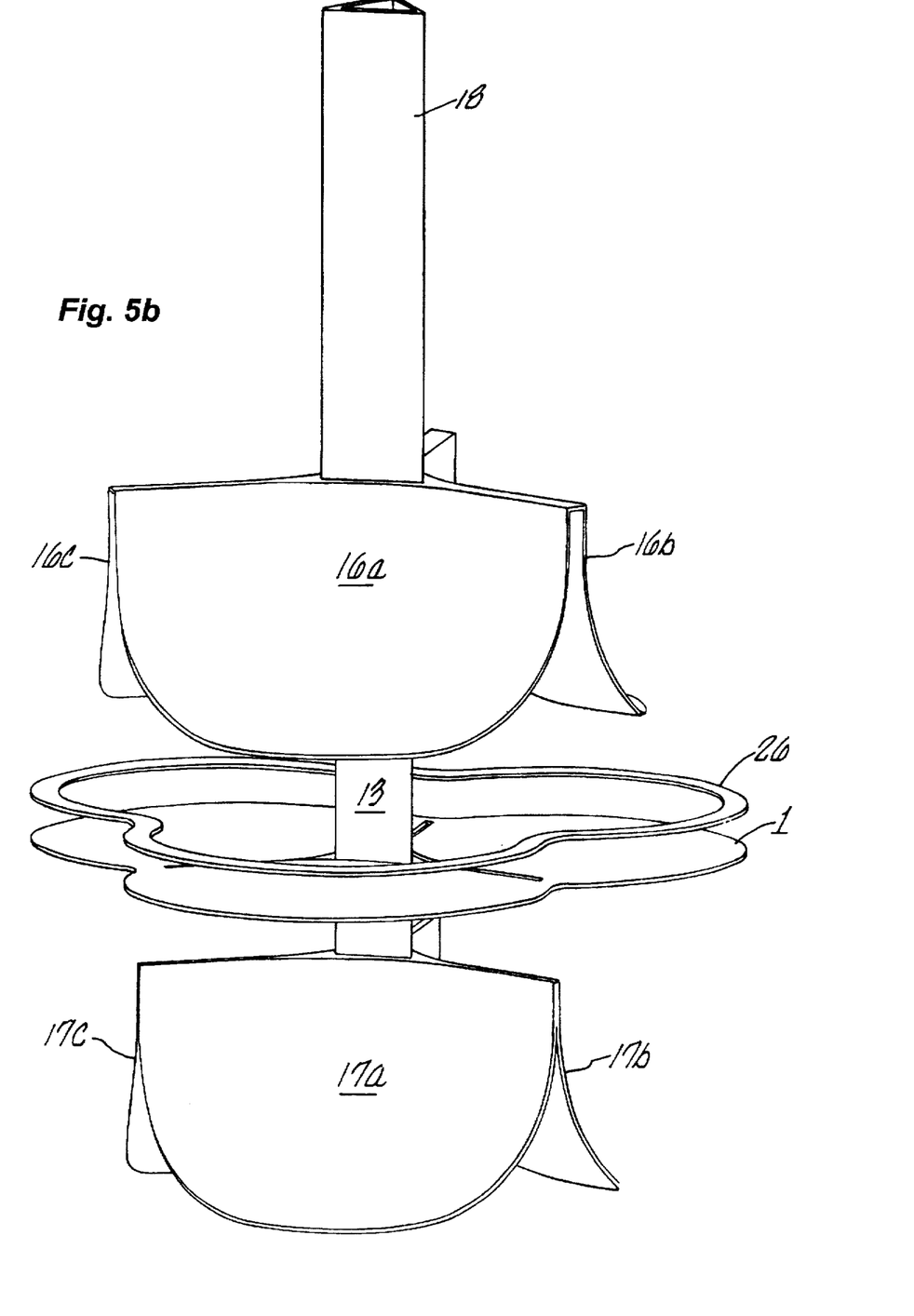
Figure 5C:
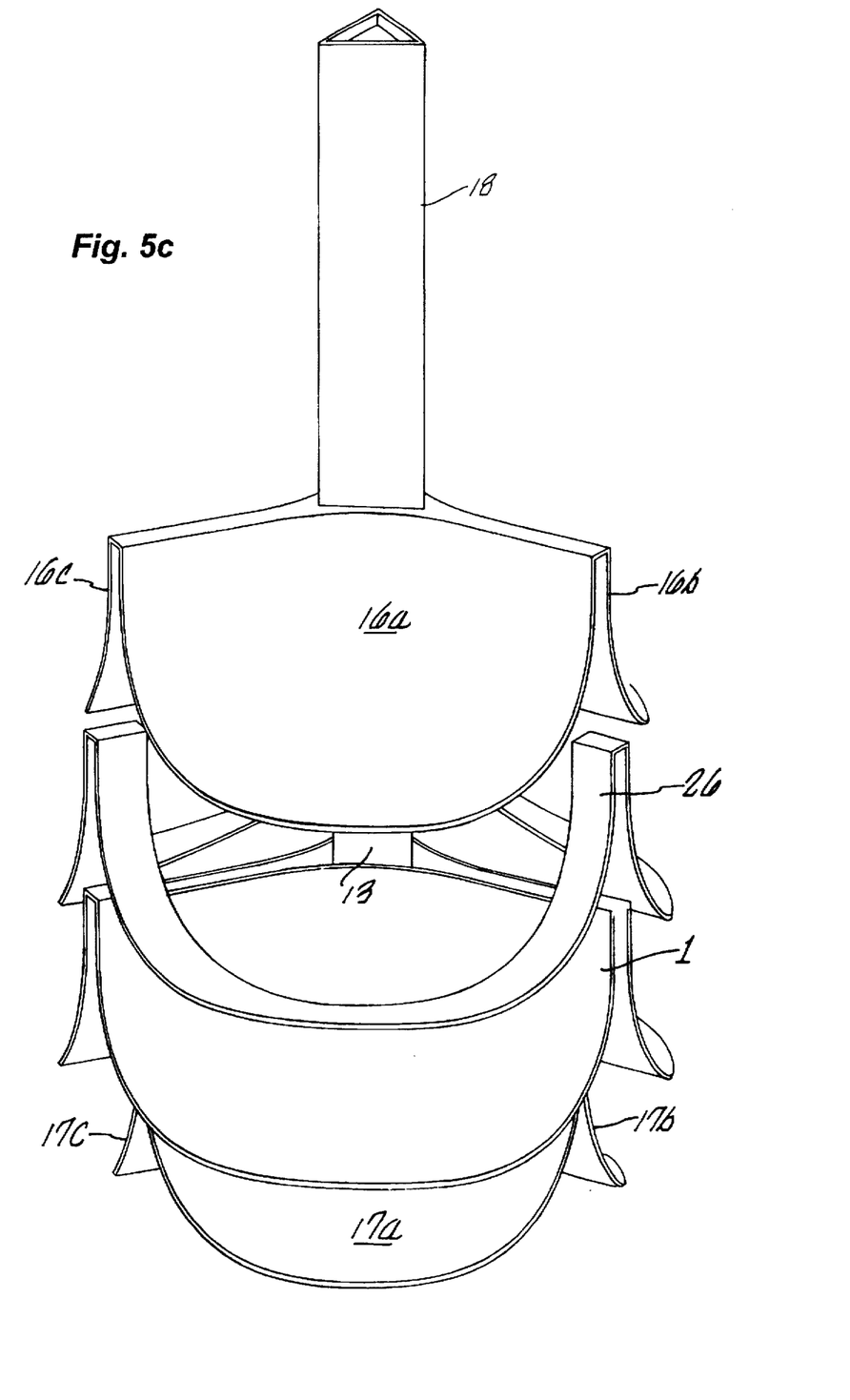

FIGS. 5b and 5c illustrate one method of utilizing the pledger 26 in the context of the subject invention. As shown, the pledger 26 and trefoil pattern are both inserted between the blades of the upper and lower formers in the manner described previously. Then, the lower former is fully inserted into the upper former, and the two are placed in an engaging relationship such that the trefoil pattern 1 forms a tri-leaflet valve structure and the continuous pledget 26 forms a shape which matches that of the outer periphery of the base of the tri-leaflet valve structure formed from the trefoil pattern. Advantageously, the pledger 26 is at least partially situated over the edge portion extending around the outer periphery of the base of the tri-leaflet valve structure. The result is to form a reinforced edge portion. At this point, sutures are then utilized to secure the reinforced edge portion to the exposed annulus.

Figures 5D, 5E:
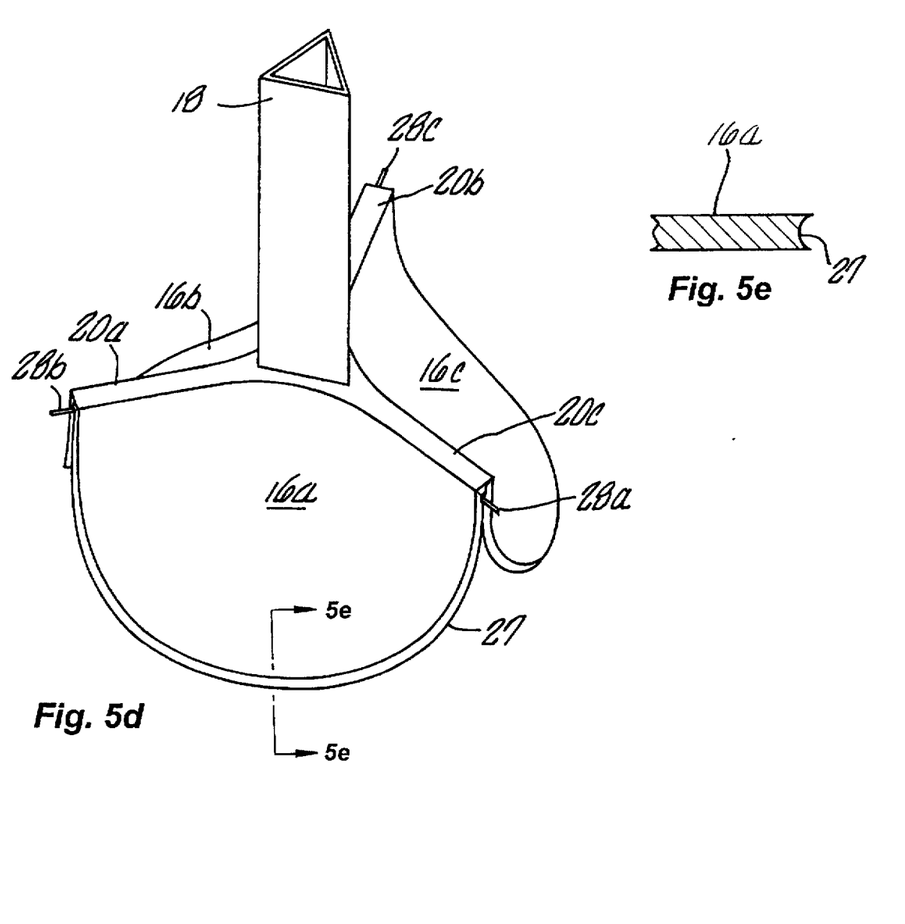

Another approach for utilizing a pledger in the context of the subject invention is illustrated in FIGS. 5d and 5e. As shown, the blades of the upper former are configured with a groove 27 configured for at least partial insertion of pledger 26. A side view of the groove is shown in FIG. 5e. The depth of the groove is such that the pledger protrudes at least partly beyond the edge of the former. Pins, identified with numerals 28a, 28b, and 28c, are also provided at the commissure areas 20a, 20b, and 20c of the upper former. The pledget is inserted into the groove 27 and looped over the pins 28a, 28b, and 28c. After the repaired valve has been secured in place, the pledget is disengaged from the pins, and the upper former is withdrawn from the repair site as described previously.

While embodiments and applications of this invention have been shown and described, it should be apparent to those of ordinary skill in the art that the these examples are merely illustrative, and that many embodiments are possible without departing from the spirit and scope of the subject invention. Specifically, it should be appreciated that the subject invention can be used to repair less than all, i.e., one or two, leaflets of a discarded valve. The process would involve forming a precut pattern comprising only one or two of the lobes shown in FIG. 1, and using the resultant tissue to repair the valve in the manner described, except that only the one or two prescribed leaflets in the native valve would be excised and repaired. Accordingly, the invention is not to be restricted, except as by the appended claims.

What is claimed is:

1. A method for repairing a heart valve comprising:
   (a) sizing an annulus of a heart;
   (b) harvesting tissue;
   (c) cutting a trefoil pattern matched to the size of the annulus from the harvested tissue;
   (d) forming a valve having at least one leaflet from said trefoil pattern, the valve having a base with an edge portion of tissue extending around an outer periphery thereof; and
   (e) suturing the edge portion to the exposed annulus.

2. The method of claim 1 wherein said harvesting step comprises harvesting autologous tissue.

3. The method of claim 2 wherein said harvesting step comprises harvesting pericardium.

4. The method of claim 2 further comprising the step of immersing said harvested tissue in a glutaraldehyde solution.

5. The method of claim 1 wherein said forming step comprises molding the pattern into the valve using a pair of engageable formers.

6. The method of claim 5 wherein the formers are molded in a three-dimensional shape representative of a partially closed tri-leaflet valve.

7. The method of claim 5 wherein the formers are planar.

8. The method of claim 5 wherein said forming step further comprises exposing said edge portion of tissue.

9. The method of claim 1 wherein said cutting step comprises cutting the pattern from the harvested tissue using a size specific tissue cutting die.

10. The method of claim 1 further comprising the step of reinforcing the edge portion of tissue with a pledget made from a bio-compatible material.

11. The method of claim 5 further comprising providing a pre-fabricated kit in which is contained said pair of formers.

12. The method of claim 1 wherein the pattern is a trefoil pattern, and the valve is a tri-leaflet valve.

13. The method of claim 1 wherein the pattern has less than three lobes, and the valve has less than three leaflets.

14. A method of repairing a heart valve comprising the steps of:

(a) sizing an annulus of a heart at a repair site;

(b) harvesting tissue;

(c) cutting a trefoil pattern from the harvested tissue specific to the size of the annulus;

(d) providing first and second formers which are specific to the size of the annulus of the valve, (e) forming a tri-leaflet valve from said trefoil pattern by engaging blades of said first former to corresponding blades of said second former with said trefoil pattern sandwiched therebetween;

(f) exposing an edge portion of tissue extending around an outer periphery of a base of the valve;

(g) moving the formers with the trefoil pattern sandwiched therebetween to a position which is proximate to the repair site;

(h) suturing the exposed edge portion to the annulus; and (i) withdrawing the formers from the repair site.

15. The method of claim 14 wherein said harvesting step comprises harvesting autologous tissue.

16. The method of claim 15 wherein said step of harvesting tissue comprises harvesting pericardium.

17. The method of claim 15 further comprising the step of immersing said harvested tissue in a glutaraldehyde solution.

18. The method of claim 14 wherein said cutting step comprises cutting said trefoil pattern out of said harvested tissue using a size specific tissue cutting die.

19. The method of claim 14 further comprising reinforcing the exposed strip of tissue with a pledget made of a bio-compatible material.

20. The method of claim 14 further comprising providing a size specific pre-fabricated kit in which said formers are contained.

21. The method of claim 18 further comprising providing a pre-fabricated kit in which is contained said size specific tissue cutting die.

22. A method of repairing a heart valve comprising the steps of:

(a) sizing an annulus of a heart at a repair site;

(b) harvesting autologous tissue;

(c) cutting a unitary trefoil pattern from the harvested tissue, the trefoil pattern having three lobes arranged in substantial radial symmetry about a central coaption point within a central aperture, the central aperture having coaptive edges which meet at the central coaption point when the valve is in a closed position;

(d) providing a pre-fabricated kit containing size specific first and second formers;

(e) engaging blades of the first former with corresponding blades of the second former with the trefoil pattern sandwiched therebetween to form a tri-leaflet valve;

(f) exposing an edge portion of tissue extending around an outer periphery of a base of the valve;

(g) moving the formers with the trefoil pattern sandwiched therebetween to a position which is proximate to the repair site;

(h) suturing the edge portion to the annulus; and (i) withdrawing the formers from the valve repair site.

23. The method of claim 22 wherein said harvesting step comprises harvesting pericardium.

24. The method of claim 22 wherein said cutting step comprises cutting said trefoil pattern from said harvested tissue using a size specific tissue cutting die.

25. The method of claim 24 further comprising containing said size specific tissue cutting die in said pre-fabricated kit.

26. The method of claim 22 further comprising retracting the blades of said lower former.

27. The method of claim 22 wherein said cutting step further comprises cutting said trefoil pattern such that the lobes meet adjacent lobes at commissure areas, and are configured with extra coaptive surfaces such that the central coaption point lies above a plane defined by the commissure areas.

* * * * *